US012131248B2

(12) United States Patent
Li et al.

(10) Patent No.: US 12,131,248 B2
(45) Date of Patent: Oct. 29, 2024

(54) GRAPH NEURAL NETWORK SYSTEMS FOR GENERATING STRUCTURED REPRESENTATIONS OF OBJECTS

(71) Applicant: DeepMind Technologies Limited, London (GB)

(72) Inventors: Yujia Li, London (GB); Christopher James Dyer, London (GB); Oriol Vinyals, London (GB)

(73) Assignee: DeepMind Technologies Limited, London (GB)

( * ) Notice: Subject to any disclaimer, the term of this patent is extended or adjusted under 35 U.S.C. 154(b) by 0 days.

(21) Appl. No.: 18/144,810

(22) Filed: May 8, 2023

(65) Prior Publication Data

US 2024/0054328 A1 Feb. 15, 2024

Related U.S. Application Data

(63) Continuation of application No. 16/759,525, filed as application No. PCT/EP2018/079556 on Oct. 29, 2018, now Pat. No. 11,704,541.

(60) Provisional application No. 62/578,301, filed on Oct. 27, 2017.

(51) Int. Cl.
*G06N 3/04* (2023.01)
*G06F 16/901* (2019.01)
*G06F 17/18* (2006.01)
*G06N 3/045* (2023.01)
(Continued)

(52) U.S. Cl.
CPC ......... *G06N 3/047* (2023.01); *G06F 16/9024* (2019.01); *G06F 17/18* (2013.01); *G06N 3/045* (2023.01); *G06N 3/08* (2013.01)

(58) Field of Classification Search
CPC ...... G06N 3/0472; G06N 3/0454; G06N 3/08; G06F 16/9024; G06F 17/18
See application file for complete search history.

(56) References Cited

U.S. PATENT DOCUMENTS

| 11,023,817 | B2 * | 6/2021 | Katsuki | G06N 7/01 |
| 2004/0230397 | A1 * | 11/2004 | Chadwick | G06Q 10/10 702/181 |
| 2017/0177943 | A1 * | 6/2017 | Mehrseresht | G06V 10/85 |

(Continued)

FOREIGN PATENT DOCUMENTS

| CN | 106471525 | 3/2017 |
| CN | 106471526 | 3/2017 |

(Continued)

OTHER PUBLICATIONS

Johnson DD. Learning graphical state transitions. InInternational conference on learning representations Oct. 29, 2016. (Year: 2016).*

(Continued)

*Primary Examiner* — Fayyaz Alam
(74) *Attorney, Agent, or Firm* — Fish & Richardson P.C.

(57) ABSTRACT

There is described a neural network system for generating a graph, the graph comprising a set of nodes and edges. The system comprises one or more neural networks configured to represent a probability distribution over sequences of node generating decisions and/or edge generating decisions, and one or more computers configured to sample the probability distribution represented by the one or more neural networks to generate a graph.

20 Claims, 6 Drawing Sheets

(51) Int. Cl.
G06N 3/047 (2023.01)
G06N 3/08 (2023.01)

(56) References Cited

U.S. PATENT DOCUMENTS

| | | | | |
|---|---|---|---|---|
| 2018/0025291 | A1* | 1/2018 | Dey | G06N 7/01 |
| | | | | 706/11 |
| 2018/0173955 | A1* | 6/2018 | Mehrseresht | G06F 18/24137 |
| 2020/0026999 | A1* | 1/2020 | Wang | G06N 3/063 |

FOREIGN PATENT DOCUMENTS

| | | |
|---|---|---|
| CN | 106503055 | 3/2017 |
| CN | 106777125 | 5/2017 |
| CN | 106874688 | 6/2017 |
| CN | 106960415 | 7/2017 |

OTHER PUBLICATIONS

Buesing L, Bill J, Nessler B, Maass W. Neural dynamics as sampling: a model for stochastic computation in recurrent networks of spiking neurons. PL oS computational biology. Nov. 3, 2011;7(11):e1002211. (Year: 2011).*

Su CT, Chou Cj. A neural network-based approach for statistical probability distribution recognition. Quality Engineering. Sep. 1, 2006;18(3):293-7. (Year: 2006).*

Aguiñaga et al., "Growing graphs from hyperedge replacement graph grammars," Proceedings of the 25th ACM International on Conference on Information and Knowledge Management, 2016, pp. 469-478.

Barabási et al., "Emergence of scaling in random networks," Science, 1999, 286(5439):509-512.

Battaglia et al., "Interaction networks for learning about objects, relations and physics," Advances in Neural Information Processing Systems 29, 2016, 9 pages.

Bjerrum et al., "Molecular generation with recurrent neural networks," CoRR, 2017, arXiv:1705.04612, 9 pages.

Bjerrum et al., "Smiles enumeration as data augmentation for neural network modeling of molecules," CoRR, 2017, https://arxiv.org/abs/1703.07076, 7 pages.

Droste et al., "Weighted automata and weighted logics," Theoretical Computer Science, 2007, 380(1-2):69-86.

Duvenaud et al., "Convolutional networks on graphs for learning molecular fingerprints," Advances in neural information processing systems, 2015, 9 pages.

Dyer et al., "Recurrent neural network grammars," CoRR, 2016, arXiv preprint arXiv:1602.07776, 13 pages.

Erdos et al., "On the evolution of random graphs," Publ. Math. Inst. Hung. Acad. Sci, 1960, 5(1):17-60.

Esben et al., "Molecular generation with recurrent neural networks," CoRR, 2017, https://arxiv.org/abs/1705.04612, 9 pages.

Esben et al., "Smiles enumeration as data augmentation for neural network modeling of molecules," CoRR, 2017, arXiv preprint arXiv:1703.07076, 7 pages.

Gilmer et al., "Neural message passing for quantum chemistry," CoRR, 2017, https://arxiv.org/abs/1704.01212, 14 pages.

Gomez-Bombarelli et al., "Automatic chemical design using a data-driven continuous representation of molecules," ACS Cent. Sci., 2018, 4:268-276.

Henaff et al., "Deep convolutional networks on graph-structured data," CoRR, 2015, arXiv preprint arXiv:1506.05163, 10 pages.

Kingma et al., "A method for stochastic optimization," CoRR, 2014, arXiv preprint arXiv:1412.6980, 15 pages.

Kipf et al., "Semi-supervised classification with graph convolutional networks," CoRR, 2016, arXiv preprint arXiv:1609.02907, 14 pages.

Kipf et al., "Variational graph auto-encoders," CoRR, 2016, arXiv:1611.07308v1, 3 pages.

Kuhlmann et al., "Towards a catalogue of linguistic graph banks," Computational Linguistics, 2016, 42(4):819-827.

Kusner et al., "Gramnar variational autoencoder," CoRR, 2017, arXiv:1703.01925v1, 12 pages.

Lautemann, "Decomposition trees: Structured graph representation and efficient algorithms," In Proc. of the 13th Colloquium on Trees in Algebra and Programming, 1988, pp. 28-39.

Leskovec et al., "Kronecker graphs: An approach to modeling networks," Journal of Machine Learning Research, 2010, 11:985-1042.

Li et al., "Gated graph sequence neural networks," CoRR, 2016, https://arxiv.org/abs/1511.05493, 20 pages.

Maddison et al., "Structured generative models of natural source code," In Proceedings of the 31st International Conference on Machine Learning, 2014, 32:649-657.

Mallows, "Non-null ranking models," Biometrika, 1957, 44(1/2):114-130.

Margaritis, "Learning Bayesian Network Model Structure from Data," Thesis for the degree of Doctor of Philosophy, Carnegie Mellon University, School of Computer Science, May 2003, 127 pages.

Office Action in Chinese Appln. No. 201880070076.8, dated Jan. 9, 2023, 23 pages.

Office Action in European Appln. No. 18795539.8, dated Oct. 5, 2022, 8 pages.

Olivecrona et al., "Molecular de novo design through deep reinforcement learning," Journal of Cheminformatics, 2017, 9(1):14 pages.

Parisotto et al., "Neuro-symbolic program synthesis," CoRR, 2016, arXiv preprint arXiv:1611.01855, 14 pages.

PCT International Preliminary Report on Patentability in International Appln. No. PCT/EP2018/079556, mailed May 7, 2020, 9 pages.

PCT International Search Report and Written Opinion in International Appln. No. PCT/EP2018/079556, mailed Feb. 12, 2019, 15 pages.

Plackett, "The analysis of permutations," Applied Statistics, 1975, 24(2):193-202.

Scarselli et al., "The graph neural network model," IEEE Transactions on Neural Networks, Jan. 2009, 20(1):61-80.

Segler et al., "Generating focused molecule libraries for drug discovery with recurrent neural networks," ACS Cent. Sci. 2018, 4(1):120-131.

Simonovsky et al., "Graphvae: Towards generation of small graphs using variational autoencoders," International Conference on Artificial Neural Networks, Artificial Neural Networks and Machine Learning, 2018, pp. 412-422.

Socher et al., "Parsing natural scenes and natural language with recursive neural networks," In Proceedings of the 28th international conference on machine learning, 2011, pp. 129-136.

Stewart et al., "End-to-end people detection in crowded scenes," Proceedings of the IEEE Conference on Computer Vision and Pattern Recognition, 2016, pp. 2325-2333.

Vinyals et al., "Grammar as a foreign language," Advances in Neural Information Processing Systems, 2015, pp. 2773-2781.

Vinyals et al., "Order Matters: Sequence to sequence for sets," CoRR, 2015, arxiv.org/abs/1511.06391, 11 pages.

Vinyals et al., "Pointer networks," Advances in Neural Information Processing Systems, 2015, pp. 2692-2700.

Watts et al., "Collective dynamics of 'small-world' networks," Nature, 1998, 393(6684):440-442.

www.rdkit.org [online], "RDKit: Open-Source Cheminformatics Software," 2006, retrieved on Jul. 23, 2020, retrieved from URL<http://www.rdkit.org>, 2 pages.

Yujia et al., "Gated graph sequence neural networks," CoRR, 2016, https://arxiv.org/abs/1511.05493, 20 pages.

Office Action in European Appln. No. 18795539.8, dated Mar. 13, 2024, 6 pages.

* cited by examiner

GRAPH NEURAL NETWORK SYSTEMS FOR GENERATING STRUCTURED REPRESENTATIONS OF OBJECTS

CROSS-REFERENCE TO RELATED APPLICATIONS

This application is a continuation of U.S. application Ser. No. 16/759,525, filed on Apr. 27, 2020, which is a National Stage Application under 35 U.S.C. § 371 and claims the benefit of International Application No. PCT/EP2018/079556, filed on Oct. 29, 2018, which claims priority to U.S. Provisional Application No. 62/578,301, filed on Oct. 27, 2017. The disclosures of the prior applications are considered part of and are incorporated by reference in the disclosure of this application.

BACKGROUND

This specification relates to generative neural network systems using graph neural networks structured representations of objects and entities, in particular physical entities.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

Some neural networks are recurrent neural networks. A recurrent neural network is a neural network that receives an input sequence and generates an output sequence from the input sequence. In particular, a recurrent neural network can use some or all of the internal state of the network from a previous time step in computing an output at a current time step. An example of a recurrent neural network is a long short term (LSTM) neural network that includes one or more LSTM memory blocks. Each LSTM memory block can include one or more cells that each include an input gate, a forget gate, and an output gate that allow the cell to store previous states for the cell, e.g., for use in generating a current activation or to be provided to other components of the LSTM neural network.

Some neural networks represent graph structures comprising nodes connected by edges; the graphs may be multigraphs in which nodes may be connected by multiple i.e. bidirectional edges. The nodes and edges may have associated node features and edge features; these may be updated using node functions and edge functions, which may be implemented by neural networks.

SUMMARY

This specification describes a neural network system implemented as computer programs on one or more computers in one or more locations that implements a generative model of graphs which may be used to generate new graphs. Graph structures may be used to represent many different types of physical systems and entities. A system capable of generating arbitrary graphs having specified properties provides an all-purpose system capable of solving many technical problems involving real-world physical entities. For example, a graph may represent a drug molecule and the system may be used to generate new potentially viable drugs; a graph may represent a computer network and the system may be used to generate a computer network design have certain latency, bandwidth and quality of service requirements; a graph may represent a transportation network and the system may be used to generate an efficient transportation network; a graph may represent a computer chip (with nodes representing chip components or structures and edges representing connections between those components or structures) and the system may be used to generate chip designs with lower latencies or lower power consumption. In further examples, a graph may represent a warehouse layout and may be used for control of a robotic system in the warehouse; a graph may represent an item of manufacture and may be used to control a robotic system to assemble, disassemble or repair the item; a graph may represent a physical location and may be used by an autonomous agent such as a self-driving vehicle to navigate through the physical location. It will be appreciated that there exists many other technical applications for generated graph structures.

In general, a graph comprises a set of nodes and a set of edges that connect two nodes. It is possible however, for graphs to have only unconnected nodes with no edges or in a special case, for a graph to contain no nodes and no edges.

A node of a graph may be used to represent a particular entity in a physical system and may have a type based upon a type of the entity. For example, a node may represent a particular atom of a molecule, the atom being of a particular type of chemical element. A feature vector may be associated with a node. The feature vector may represent the type of node and other properties of the entity represented by the node.

An edge of a graph may be used to represent a relationship between two nodes connected by the edge. For example, an edge may represent a chemical bond between two atoms or may represent communication link between two nodes of a network. Edges may also have a type associated, for example, if a communication link is a wired or wireless link. A feature vector may be associated with an edge. The feature vector may represent the type of edge and other properties associated with the edge. Edges may be directed or undirected. An undirected edge may be represented using a pair of directed edges having opposing directions.

According to an aspect, there is described a neural network system for generating a graph, the graph comprising a set of nodes and edges, the system comprising: one or more neural networks configured to represent a probability distribution over sequences of node generating decisions and/or edge generating decisions; and one or more computers configured to sample the probability distribution represented by the one or more neural networks to generate a graph.

In this way, a graph may be modelled as a sequence of node and/or edge generating decisions by one or more neural networks. The system is capable of modelling arbitrary graph structures having any number of properties. A new graph having properties similar to the modelled properties may be generated by sampling from the probability distribution represented by the one or more neural networks.

Aspects may include one or more of the following features.

The one or more neural networks may comprise: a node creation neural network configured to receive as input a graph and output one or more probabilities of adding a new node to the graph; an edge addition neural network configured to receive as input a graph and an indication of a candidate node and output one or more probabilities of adding an edge connected to the candidate node to the graph; a node selection neural network configured to receive as input a graph and an indication of a candidate node and output one or more probabilities of adding an edge to the graph between the candidate node and each of the nodes of the graph; and wherein sampling the probability distribution to generate a graph may further comprise: generating a node of the graph based upon the output of node creation neural network; and generating an edge of the graph based upon the output of the edge addition neural network and the node selection neural network.

In this way, the model comprises separate neural networks or neural network subsystems for modelling each part of the graph generation sequence. In particular, a node creation neural network models the decision process for determining whether to add a new node to a graph. The edge addition neural network models the decision process of determining whether to add an edge to a node of the graph, and the node selection neural network models the decision process of determining to which node an additional edge should be connected. Each of the neural networks receives as input a graph, that is, the neural network may receive the graph currently under construction. As such, the decisions as to whether to add nodes, edges and selections of nodes is based upon an up-to-date state of the graph under construction and the history of decisions made in generating the current graph. In this way, one decision may feed into the next.

The one or more computers may be further configured to generate a graph based upon an iterative process of generating a node and generating an edge wherein generating an edge occurs subsequent to generating a node. That is, generating a graph may comprise the repeating steps of generating a node followed by generating an edge.

Each node and each edge may be sequentially generated one at a time. In this way, multi-modal cases may be handled more easily than if all nodes and/or edges were generated simultaneously.

Generating a node of the graph may further comprise receiving an initial graph; providing the initial graph to the node creation neural network; receiving an output from the node creation neural network and determining whether a new node of the graph is to be generated based upon the output of the node creation neural network. Responsive to determining that a new node of the graph is to be generated: generating the new node; and generating an updated graph by updating the initial graph to include the new node. Responsive to determining that a new node of graph is not be generated: not updating the initial graph. If no node is generated, then it may be considered that the graph generation process is complete and the system may output the initial graph unchanged.

Generating an edge of the graph may further comprise: providing the updated graph and an indication of the new node to the edge addition neural network; receiving an output from the edge addition neural network; determining whether an edge connected to the new node is to be generated based upon the output of the edge addition neural network; responsive to determining that an edge is to be generated: providing the updated graph and an indication of the new node to the node selection neural network; receiving an output from the node selection neural network; selecting a node of the graph based upon the output of the node selection neural network; and updating the graph to include an edge between the new node and the selected node. That is, the updated graph resulting from the processing by the node creation neural network is provided as an input for determining whether to then add an edge to the newly generated node.

Generating an edge of the graph may further comprise providing the updated graph and an indication of the new node to the edge addition neural network module; receiving an output from the edge addition neural network module; determining whether an edge connected to the new node is to be generated based upon the output of the edge addition neural network module; responsive to determining that an edge is to be generated: providing the updated graph and an indication of the new node to the node selection neural network module; receiving an output from the node selection neural network module; selecting a node of the graph based upon the output of the node selection neural network; and updating the graph to include an edge between the new node and the selected node. The selected node may be a different node of the graph than the new node or the selected node may be the same node as the new node. If the selected node is the same node as the new node, the edge may be a self-loop. Following the generation of an edge, it may be determined whether further edges are to be generated in a similar manner as discussed above using the updated graph including the new edge as input.

Generating an edge of the graph may further comprise determining whether to generate a further edge connected to the new node. The one or more computers may be further configured to provide the updated graph as input to the node creation neural network for generating a further node subsequent to generating an edge. As discussed above, generating a graph may be an iterative process, and further nodes may be generated in a similar manner discussed above using the updated graph as input.

Each node of the graph may be associated with information and the one or more computers may be configured to propagate information between neighboring nodes to provide a node with information from the local neighborhood of the node. In this way, changes in the structure of the graph or other properties of the graph may be communicated to nodes. In addition, or alternatively, such propagation of information may be carried out by any one of the one or more neural networks. A local neighborhood of a node may be the set of nodes directly connected to the node.

The one or more computers may be configured to perform a plurality of rounds of information propagation. In this way, with each round, information from more distant nodes outside of the local neighborhood of a node may be propagated towards the node, eventually reaching the node if sufficient rounds are performed.

The information associated with a node may be encoded as a state vector. Propagating information between neighbouring nodes may comprise generating a message vector associated with an edge connecting the neighbouring nodes based upon the state vectors associated with the neighbouring nodes. The message vector may be further based upon a feature vector associated with the edge. The feature vector may be based upon an edge type. The message vector may be generated using a neural network.

Propagating information to a node further comprises updating a state vector of the node based upon an aggregation of one or more message vectors associated with one or more edges connected to the node. The aggregation may be a summation.

The aggregation of one or more message vectors may be an aggregation of the message vectors associated with the incoming edges connected to the node. That is, information may be pulled in towards a node along all incoming directions.

The aggregation of one or more message vectors may be an aggregation of the message vectors associated with each of the edges connected to the node. That is, the aggregation may be an aggregation of message vectors associated with incoming and outgoing edges connected to the node. For an undirected graph, this includes message vectors associated with each edge connected to the node.

Updating a state vector of a node may be based upon the output of a neural network configured to receive the aggregation of message vectors and the current state vector of the node as input. The neural network may be a recurrent neural network, for example an LSTM or a Gated Recurrent Unit (GRU).

The graph may be associated with a graph state vector, wherein the graph state vector is based upon an aggregation of a set of node state vectors. The set of node state vectors may include all of the node state vectors of the all of the nodes of the graph. Aggregating a set of node state vectors may comprise: for each node state vector of the set, generating a modified node state vector by a neural network configured to receive a node state vector as input; and aggregating the set of modified node state vectors.

The modified node state vector may be of a higher dimensionality than the unmodified node state vector. In this way, the information contained by the graph state representation may comprise more information than a node state representation.

Aggregating the set of modified node state vectors may be based upon a gated sum. In addition, the gated sum may be determined based upon a gating neural network configured to receive as input the node state vector, either modified or unmodified. Alternatively, the aggregation may be based upon other reduction operators such as a mean or a maximum operation.

The node creation neural network may be further configured to: perform at least one round of propagating information between neighbouring nodes; determine a graph state vector associated with the graph; process, by a neural network, the graph state vector to determine the one or more probabilities of adding a new node to the graph.

The one or more probabilities may comprise a probability for each of a plurality of node types. As such, the system may support nodes of different types and determining whether to generate a node may include determining what type of node to generate.

The edge addition neural network may be further configured to: perform at least one round of propagating information between neighbouring nodes; determine a graph state vector associated with the graph; process, by a neural network, the graph state vector and the state vector associated with the candidate node to determine the one or more probabilities of adding an edge connected to the candidate node to the graph.

The one or more probabilities may comprise a probability for each of a plurality of edge types. As such, the system may support edges of different types and determining whether to add an edge may include determining what type of edge to add.

The node selection neural network may be further configured to: perform at least one round of propagating information between neighbouring nodes; determine, a plurality of probabilistic scores for adding an edge between candidate pairs of nodes, a candidate pair of nodes comprising the candidate node and a node of the graph, based upon processing, by a neural network, the state vectors associated with each respective node of the candidate pair of nodes. The plurality of probabilistic scores may also comprise a score for each available edge type for connecting a candidate node and a node of the graph. As such, the node selection neural network may also determine the type of edge used to connect a candidate node and a node of the graph.

The neural network system may further comprise a node initialization neural network configured to initialize the state vector of a newly generated node, wherein initializing the state vector of a newly generated node comprises: processing, by a neural network, a graph state vector and a feature vector associated with the newly generated node to determine the initial state vector. The feature vector associated with the node may be based upon a node type associated with the node.

The probability distribution represented by the one or more neural networks may be determined based upon a conditional probability distribution. The conditional probability distribution may be conditioned on data retrieved from a memory, the data retrieval based upon a memory look-up using a representation of at least a portion of the graph. That is, at least a portion of the graph may be used to compute query vector to query a memory. The graph state vector may be used to query the memory. The conditioning may be based upon an attention mechanism.

The one or more neural networks may be trained based upon maximizing an expected log-likelihood of a training dataset of graphs. In this way, the one or more neural networks may be trained in an efficient manner.

The one or more neural networks may be trained based upon a dataset of graphs, wherein each graph in the dataset is associated with an ordering of nodes and edges of the graph. For example, the ordering may be a canonical ordering associated with the graph. In addition or alternatively, the ordering may be a permutation of the canonical ordering, a random ordering or a learned ordering. The ordering may be based upon a SMILES representation of a molecule.

The one or more computers may be further configured to evaluate a graph based upon the probability distribution represented by the one or more neural networks. In this way, the properties of a generated graph may be evaluated. The properties of a generated graph may be compared to the properties of graphs in a dataset to ensure validity of the generated graph.

In some applications the graph may represent the structure of a molecule. Thus each respective node of the graph may represent an atom of the molecule or a secondary structural element of a protein such as an alpha helix or beta sheet, i.e. a part of the molecule. Each respective edge of the graph may represent an interaction between nodes such as a chemical bond between the atoms of the molecule or one or more hydrogen bonds between the secondary structural elements, i.e. chemical bonds between the parts. Thus the system may, for example, be trained on a data representing molecules and optionally their known properties. The training data may define or may be used to determine a graph representation of the molecules for training, in which both the nodes and edges are typed, e.g. according to the atoms and their bond types. The trained system may then be used to generate graphs representing other physically realistic molecules, optionally with the same or similar properties to those in the training data. As such, the system may be applied to drug discovery. The one or more neural networks may be trained based upon a metric comprising a chemical property. The one or more computers may be further configured to evaluate a graph based upon a metric comprising a chemical property, that is, one or more chemical metrics may be used to assess the quality of a sample from the model. Optionally a generated molecule may be evaluated by evaluating the molecule in silico or by synthesizing and testing the molecule in vitro or in vivo.

The one or more neural networks may further comprise a bias adjustable to alter a property associated with a graph being generated subsequent to completion of training of the one or more neural networks. For example, adjusting the bias may alter the graph size and/or edge density. For example, by changing a bias parameter in an add node neural network function the number of nodes may be changed; by changing a bias parameter in an add edge neural network function the density of edges may be changed.

According to a further aspect, there is described a method of generating a graph, the graph comprising a set of nodes and edges, the method comprising: sampling a probability distribution over sequences of node and edge generating decisions to generate a graph, the probability distribution being parameterized by one or more neural networks.

According to a further aspect, there is described a method of drug discovery comprising: generating a graph representing a drug molecule using a neural network system as described above. In this way, candidate drugs having particular desirable properties may be discovered in a manner that is more efficient than prior art methods.

According to a further aspect, there is described a method of drug discovery comprising: generating a plurality of graphs using a neural network system as described above, each graph representing a drug molecule; selecting one of the graphs representing a drug molecule; and manufacturing the drug molecule represented by the selected graph. In this way, a drug having desirable properties may be more efficiently manufactured as the neural network system is capable of efficiently generating viable candidate drugs.

According to a further aspect, there is described a method of traffic routing comprising: generating, using the system of any preceding claim, a graph representing routing paths; and determining a route based upon the generated graph representing routing paths. The method may further comprise controlling an object to travel along the determined route. In this way, an efficient route may be generated. The traffic may be vehicular traffic. As such, vehicles may be navigated efficiently.

The traffic may be network traffic and the graph may represent routing paths in a network. In this way, more efficient routing paths may be created based upon a generated graph representing routing paths.

The neural network system described above may be further applied to generate parse trees and other graphs e.g. of linguistic structures for use in natural language processing and translation, or for automatic scene generation. For example the neural network system described above may be used to generate a representation of a visual scene in terms of a parse tree—a visual scene may define a tree structure in which higher nodes in the tree represent increasingly larger elements of the scene. Thus objects and object parts in the scene may be represented by nodes, and edges may define to which other objects/parts these belong. Thus generally the system may be used to generate a scene graph of the type used in graphics editing and computer games. A graph representing a visual scene may be conditioned on input data as described later, for example to generate a representation of a scene conditional on an input. In a similar manner, a parse tree representing words or word pieces in a natural language may also be conditioned on input data.

Another exemplary application includes generating a graph representing a computer chip design, and manufacturing a computer chip according to the design. In this way, a computer chip with more energy efficient interconnections and/or lower power consumption may be manufactured. Another exemplary application includes generating a graph representing a network of devices and building a network of devices (and/or connecting an existing network of devices) based upon the generated graph representing a network of devices. In this way, a network with particular desirable properties such as low latency, high bandwidth and/or quality of service may be designed and built.

The subject matter described in this specification can be implemented in particular embodiments so as to realize one or more of the following advantages.

The system may be used to capture the distribution of a particular family of graphs having particular properties, whether the family graphs relates to, for example, drug molecules, traffic, computer chip design or any other domain. The system may then generate new graphs having properties similar to the family of graphs. Where the graphs model drug molecules, for example, the system may therefore be used in task of drug discovery by training the system using a dataset of drugs and using the system to generate potential new drug-like molecules.

For example, when used to generate graphs representing physically realizable molecules the system may learn to generate examples of new molecules without explicitly needing to calculate electrostatic charges and other interactions between atoms or other parts of the molecule. These are notoriously difficult to calculate accurately and thus some implementations of the system are able to generate molecular structures faster and with less computational power and reduced memory requirements than other techniques. They may also learn to represent features which may not be well represented by explicit calculations and may thus, in some implementations, produce more physically useful molecular structures than other techniques.

In some other implementations, for example when generating representations of visual scenes, the representation may capture semantic relationships between objects/parts of objects. This can be a more useful way of representing a scene than some other techniques because it facilitates processing of the scene. For example by grouping a set of objects/parts of objects into a larger object the larger object may be manipulated as a whole, for example to move the object, operate on the object and so forth. This in turn can reduce the amount of processing and memory which would otherwise be needed to manipulate or edit an object. In a computer game a 3D scene may be processed more easily when logical relationships between objects/parts of objects are represented together, for example to move objects together. Thus some implementations of the system can automatically generate scenes in a manner which facilitates their subsequent processing and manipulation, with potentially significant savings in the memory and computing power needed for such processing/manipulation. Similar advantages apply when generating parse trees representing natural language; again such a representation may significantly reduce memory and computing requirements compared to some other approaches.

More generally the system is capable of modelling and generating arbitrary graphs and is not limited to modelling a small number of properties of graphs such as degree distribution or diameter. In addition, the model is not limited to any subclasses of graphs such as trees. The model is not limited by any strong independence assumptions and is capable of modelling richly structured graphs where small structural differences may be functionally significant, such as in the structure of molecules. The system is also capable of generating graphs having particular structural constraints such as prohibiting self-loops or restricting the number of edges between pairs of nodes.

The system is scalable given that the parameterization of the one or more neural networks may be independent of the size of the graph.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
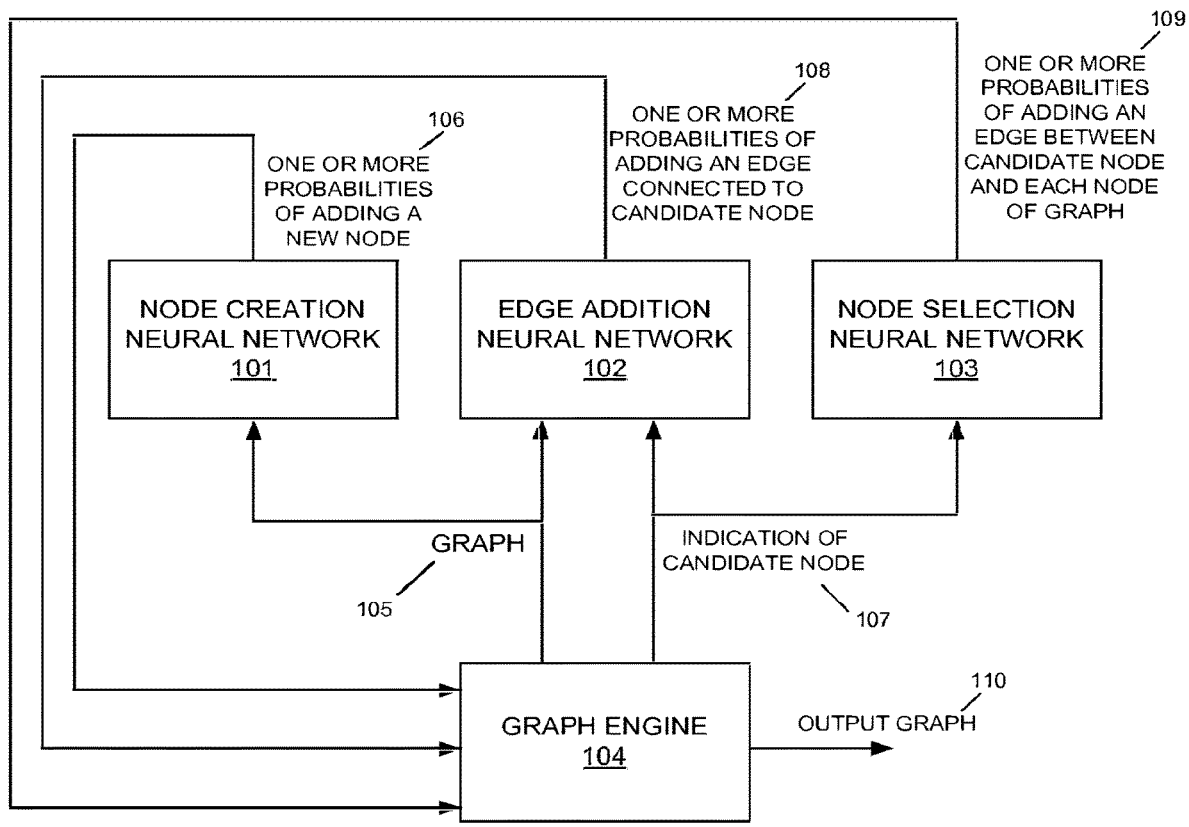
FIG. 1 shows an example neural network system for generating a graph.

FIG. 1 shows an example neural network system 100 for generating a graph. The neural network system 100 is an example of a system implemented as computer programs on one or more computers in one or more locations, in which the systems, components, and techniques described below can be implemented.

The system 100 comprises one or more neural networks configured to represent a probability distribution over sequences of node generating and edge generating decisions. In the example system 100 of FIG. 1, the one or more neural networks comprises a node creation neural network 101, an edge addition neural network 102 and a node selection neural network 103. The system 100 also comprises a graph engine 104 configured to sample the probability distribution represented by the one or more neural networks to generate a graph.

The node creation neural network 101 is configured to receive as input a graph 105 and to process the input graph 105 to output one or more probabilities 106 of adding a new node to the input graph 105. That is, the node creation neural network 101 is configured to represent a probability distribution for determining whether to add a new node to a particular graph. The input graph 105 is received from the graph engine 104 and may be a graph that is under construction by the graph engine 104. The one or more probabilities 106 of adding a new node to the input graph 105 is received by the graph engine 104 and the graph engine 104 is configured to determine whether to add a new node to the graph 105 based upon the one or more probabilities 106 of adding a new node. Where nodes are typed, the one or more probabilities 106 may comprise a probability of adding a new node of each particular type of node. The node creation neural network 101 may comprise a final softmax layer in order to provide outputs as probabilities.

The input graph 105 may have an associated graph state vector and the node creation neural network 101 may be configured to process the graph state vector to determine the one or more probabilities 106 of adding a new node. Such processing is described in more detail below.

The edge addition neural network 102 is configured to receive the input graph 105 and an indication of a candidate node 107 of the input graph 105. The edge addition neural network is further configured to process the input graph 105 and the indication of the candidate node 107 to output one or more probabilities of adding an edge 108 connected to the candidate node 107. That is, the edge additional neural network 102 is configured to represent a probability distribution for determining whether to add an edge to a node of a particular graph. The one or more probabilities 108 of adding an edge to the input graph 105 connected to the candidate node 107 are received by the graph engine 104. The graph engine 104 is configured to determine whether to add an edge connected to the candidate node 107 to the graph 105 based upon the one or more probabilities 108 of adding an edge connected to the candidate node 107. Where edges are typed, the one or more probabilities 108 may comprise a probability of adding a new edge of each particular type of edge. The edge addition neural network 102 may comprise a final softmax layer in order to provide outputs as probabilities or may comprise a final layer having a sigmoid activation function if only a single probability is required.

The edge addition neural network 102 may be configured to process a graph state representation associated with the input graph 105 and a node state vector associated with the candidate node 107 to output the one or more probabilities 108 of adding an edge connected to the candidate node 107. Such processing is described in more detail below.

The node selection neural network 103 is configured to receive the input graph 105 and an indication of the candidate node 107. The node selection neural network 103 is further configured to process the input graph 105 and the indication of the candidate node 107 to output one or more probabilities 109 of adding an edge to the graph between the candidate node 107 and each of the nodes of the graph 105. That is, the node selection neural network 103 is configured to represent a probability distribution for determining which node of a particular graph a new edge from a candidate node is to be connected to. The one or more probabilities 109 of adding an edge to the graph 105 between the candidate node 107 and each of the nodes of the graph 105 are received by the graph engine 104. The graph engine 104 is configured to determine which node of the graph 105 to add a new edge connected to the candidate node 107 in the graph 105 based upon the one or more probabilities 109 of adding an edge between the candidate node 107 and each node of the graph 105.

The node selection neural network 103 may be configured to process a node state vector associated with the candidate node 107 and a node state vector associated with each node of the input graph 105 to generate a score associated with each pairing of the candidate node 107 and a respective node of the input graph 105. The node selection neural network 103 may comprise a final softmax layer to output the one or more probabilities 109 of adding an edge between the candidate node 107 and each node of the graph 105 based upon the generated scores. The generation of scores is described in further detail below.

The node creation neural network 101, edge addition neural network 102 and node selection neural network 103 may each be a multi-layer perceptron (MLP). Alternatively, the neural networks 101, 102, 103 may be any other type of neural network having an appropriate type of activation function as deemed suitable by a person skilled in the art.

The graph engine 104 is configured to generate and output a graph 110 by sampling the probability distributions represented by the node creation neural network 101, the edge addition neural network 102 and the node selection neural network 103. Processing to generate an output graph 110 may be an iterative process. The iterative process may alternate between the steps of node generation and edge generation. An example high-level iterative process is shown in FIG. 2.

Figure 2:
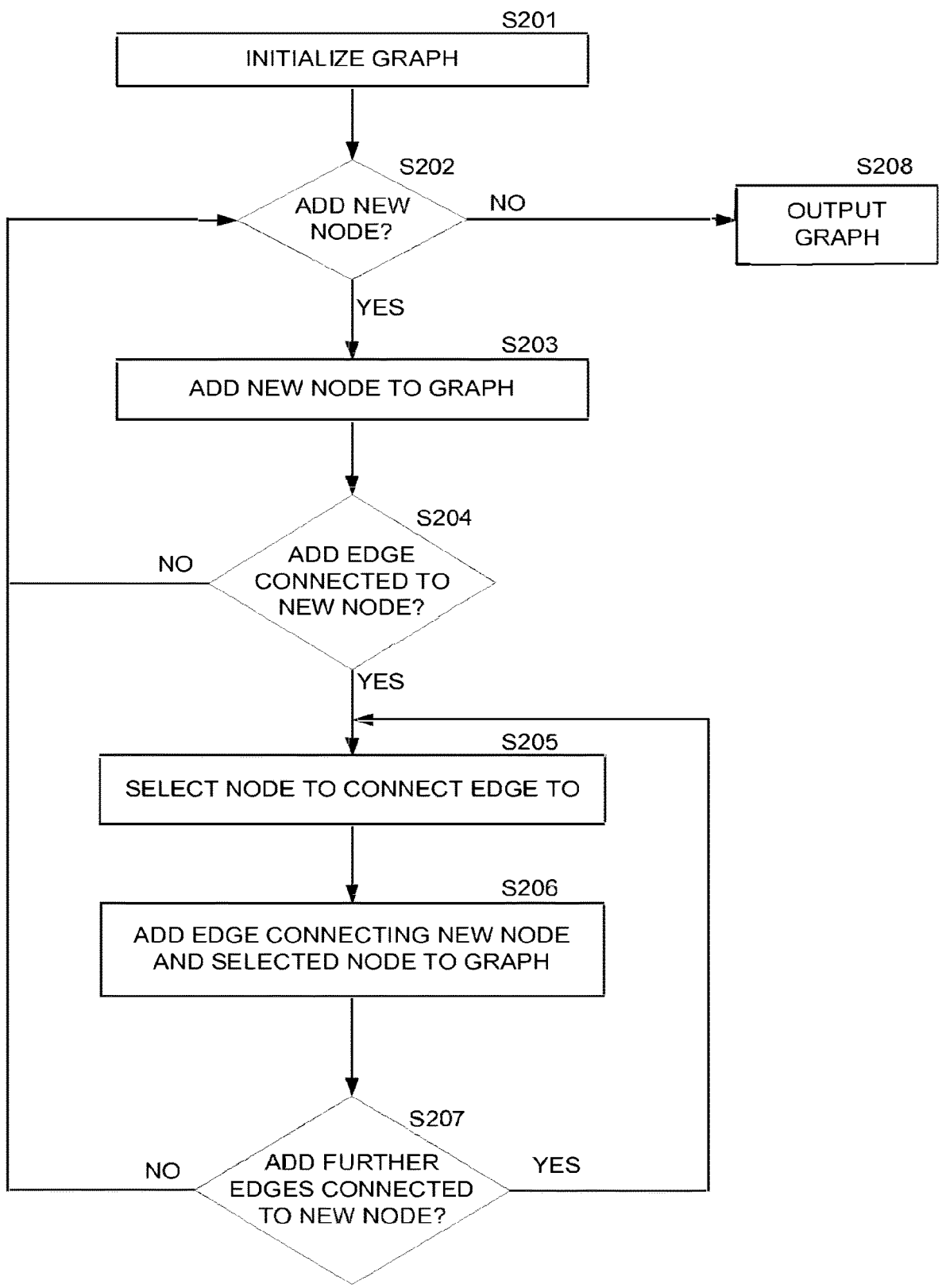
FIG. 2 shows exemplary processing for generating a graph.

At step S201 of FIG. 2, a graph comprising no nodes or edges is initialized. At step S202, it is determined whether or not to add a new node to the graph. If a node is not to be added, then the initial graph having no nodes or edges is output and the process completes. Otherwise, processing continues to step 203 where a new node is added to the graph.

At step S204, it is determined whether or not to add an edge connected to the new node. If an edge is not required, then processing returns to step S202 to determine whether further nodes are to be added to the graph. Otherwise, processing continues at step S205 to select a node of the graph to connect the new edge to. It will be appreciated that this may include the new node itself such that the graph may contain self-loops. At step S206, an edge connecting the new node and the selected node is added to the graph.

Processing then continues at step S207 where it is determined whether any further edges connected to the new node are to be generated. If further edges are required, then processing returns to step S205 to select a node to connect a further edge to. If no further edges are required, then processing returns to step S202 to determine whether any further nodes are to be generated. Thus, processing to generate nodes and edges repeat until it is determined that no further nodes are to be generated and the graph is output at step S208.

Figure 3:
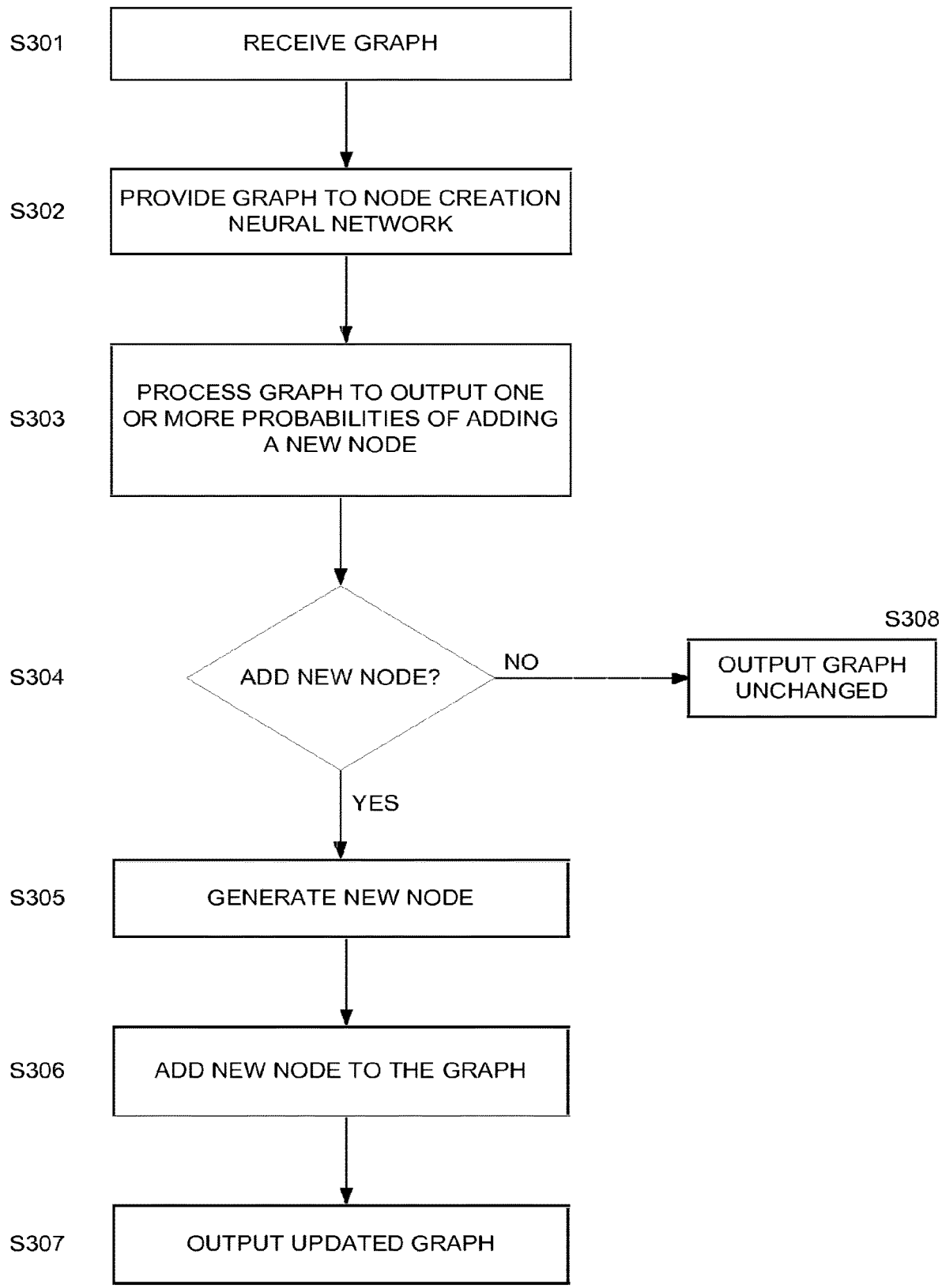
FIG. 3 shows exemplary processing for generating a node of the graph.

Referring to FIG. 3, exemplary processing for generating a node of the graph will now be described in more detail. Such processing may correspond to steps S202, S203 and S208 of FIG. 2.

At step S301, an initial or input graph 105 is received. The input graph 105 is provided to the node creation neural network 101 at step S302. The node creation neural network 101 processes the input graph 105 to output one or more probabilities 106 of adding a new node to the input graph 105 at step S303. Processing of the input graph 105 may include processing of state vectors associated with each node of the input graph 105. The processing of node state vectors may be based upon an information propagation method to update the node state vectors. An exemplary information propagation method is described in more detail below with reference to FIG. 5.

A graph state vector may be determined based upon the updated node state vectors. The one or more probabilities 106 of adding a new node to the input graph 105 may be determined based upon the graph state vector. For example, the graph state vector may be processed by the node creation neural network 101 to obtain the one or probabilities of adding a new node to the input graph 105. An exemplary method of determining a graph state vector is described in more detail below.

At step S304, it is determined whether or not a new node is to be generated based upon the one or more probabilities 106 obtained from step S303. That is, the graph engine 104 samples the probability distribution represented by the one or more probabilities 106 to determine whether or not to add a new node to input graph 105. If the nodes are typed, the sampled outcome may be a decision to add a new node of a particular type.

If it is determined that a new node is not to be added, then the input graph 105 is output unchanged at step S308. Otherwise, processing continues at step S305 to generate a new node. Generating a new node may comprise initializing a node state vector associated with the new node. The node state vector may be initialized by processing a graph state vector and a feature vector associated with the new node using a neural network. This node initialization neural network may be an MLP or any other type of suitable neural network. The feature vector associated with the new node may be based upon the type of the new node. By using both the node feature vector and the graph state vector in the initialization process, it can be ensured that different nodes having the same feature vector/type will have a different initialization dependent on the current state of the graph.

At step S306, the new node is added to the graph 105. The updated graph 105 is then output at step S307. Processing may then continue in order to add edges connecting the new node to other nodes in the graph as shown in steps S204 to S207 and described in more detail below with reference to the exemplary processing shown in FIG. 4.

Figure 4:
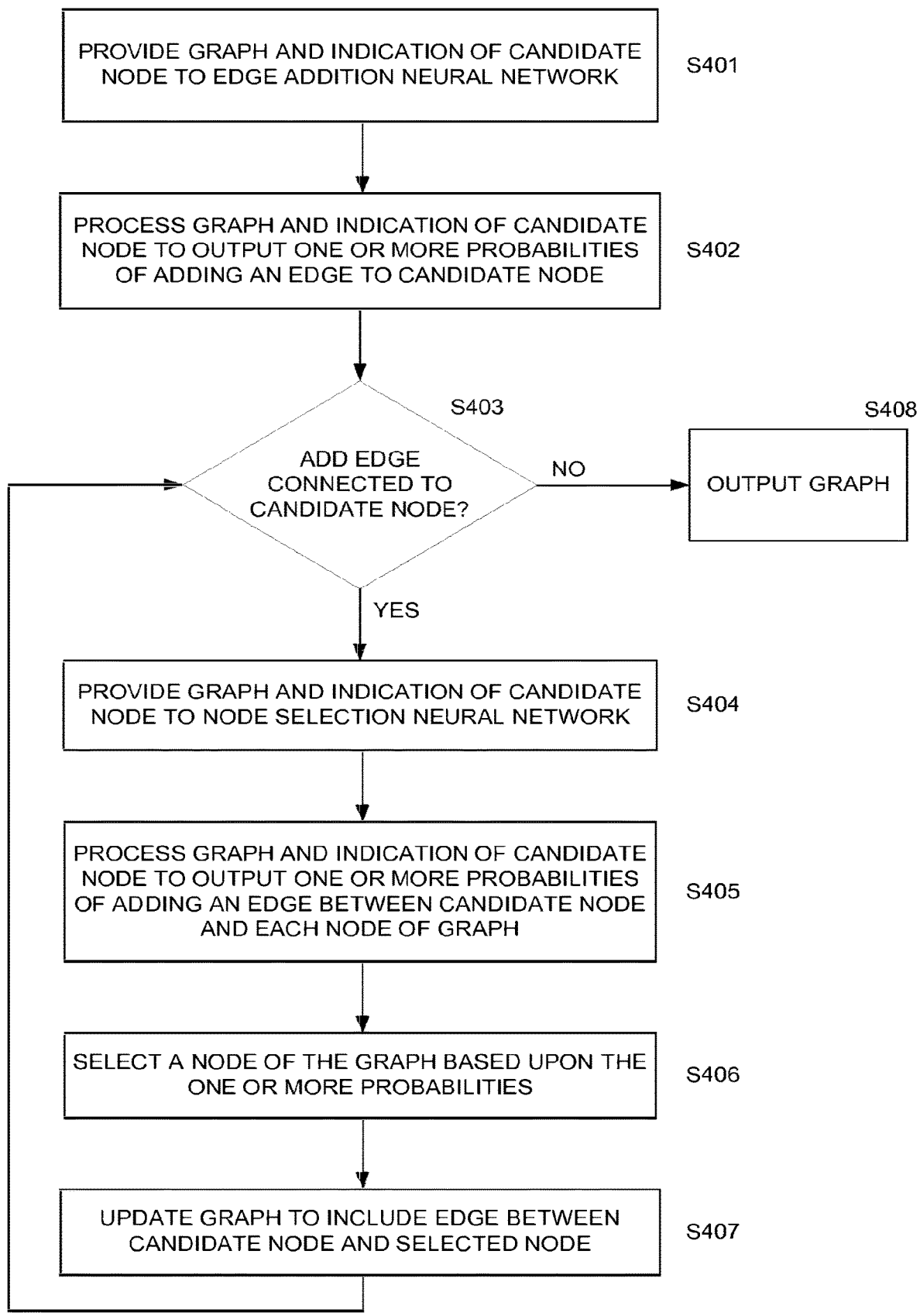
FIG. 4 shows exemplary processing for generating an edge of the graph.

At step S401 of FIG. 4, a graph such as the input graph 105 or the updated graph of step S307 is provided to the edge addition neural network 102. In addition, an indication of a candidate node 107 such as an indication of the newly generated node at step S305 is provided to the edge addition neural network 102. The edge addition neural network 102 processes the graph and the indication of a candidate node 107 to output one or more probabilities 108 of adding an edge connected to the candidate node 107 to the graph 105 at step S402.

The indication of the candidate node 107 may be a state vector associated with the candidate node 107. The node state vectors of each node in the graph 105 may be updated based upon the information propagation method mentioned above and described in more detail below with reference to FIG. 5. This ensures that information may be propagated through the graph along newly added edges from previous edge addition iterations. In particular, where a candidate node is a newly generated node, the new node is able to obtain information from its local neighborhood.

A graph state vector may be determined based upon the updated node state vectors. The one or more probabilities 108 of adding an edge connected to the candidate node 107 to the graph may be determined based upon processing of the updated node state vector associated with the candidate node 107 and the graph state vector by the edge addition neural network 102.

At step S403, it is determined whether or not an edge connected to the candidate node 107 is to be added based upon the one or more probabilities 108 obtained at step S402. That is, the graph engine 104 samples the probability distribution represented by the one or more probabilities 108 to determine whether or not to add an edge connected to the candidate node 107.

If no edges are to be added, then the graph is provided as output at step S408. Processing may then return to step S202 to determine whether further nodes are to be added to the graph 105.

If an edge is to be added, processing continues at step S404 in which the graph 105 and the indication of the candidate node 107 is provided to the node selection neural network 103. The node selection neural network 103 processes the graph 105 and the indication of the candidate node 107 to output one or more probabilities 109 of adding an edge between the candidate node 107 and each node of the graph 105. Similar to the above, the indication of the candidate node 107 may be a state vector associated with the candidate node 107 and the node state vectors of each node in the graph may be updated based upon the information propagation method. The node selection neural network 103 may process each pairing of the candidate node 107 and a respective node of the graph 105 to generate a score for adding an edge connecting the candidate node 107 and the respective node of the graph 105. Where edges have an associated type, a score may be generated for each type of edge. The node selection neural network 103 may then process the generated scores through a softmax layer to generate the one or more probabilities 109 of adding an edge between the candidate node 107 and each node of the graph.

At step S405, a node is selected based upon the one or more probabilities obtained at step S404. That is, the graph engine 104 samples the probability distribution represented by the one or more probabilities 109 to determine which node of the graph 105 to connect the candidate node 107 to. If edges are typed, the selection may also include the type of edge to be used to connect the candidate node 107 and the selected node.

The graph is then updated to include an edge between the candidate node 107 and the node selected at step S406. Processing may then return to step S403 to determine whether any further edges connecting the candidate node 107 are required.

Figure 5:
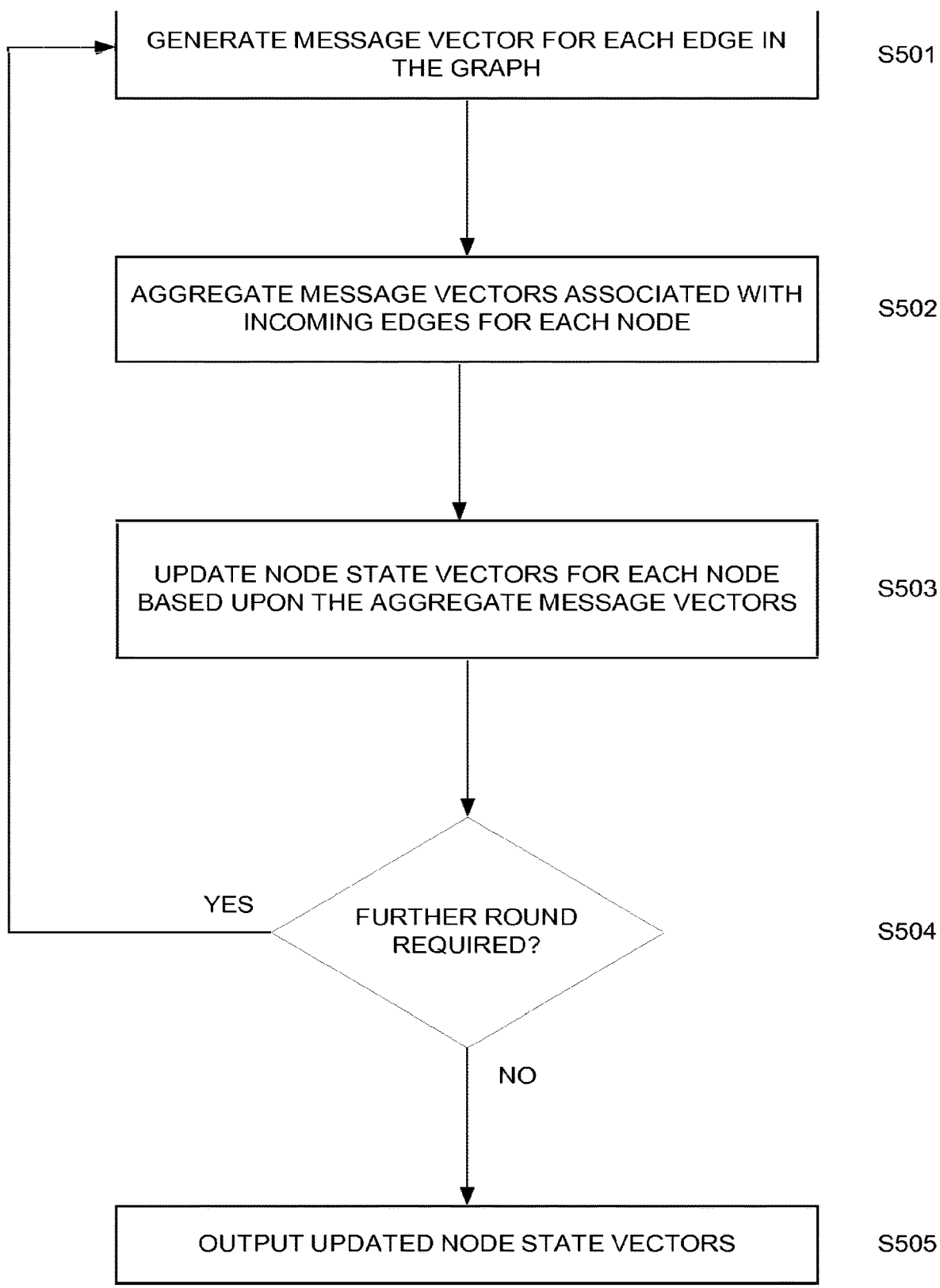
FIG. 5 shows exemplary processing for updating state vectors associated with nodes of the graph.
Figure 6:
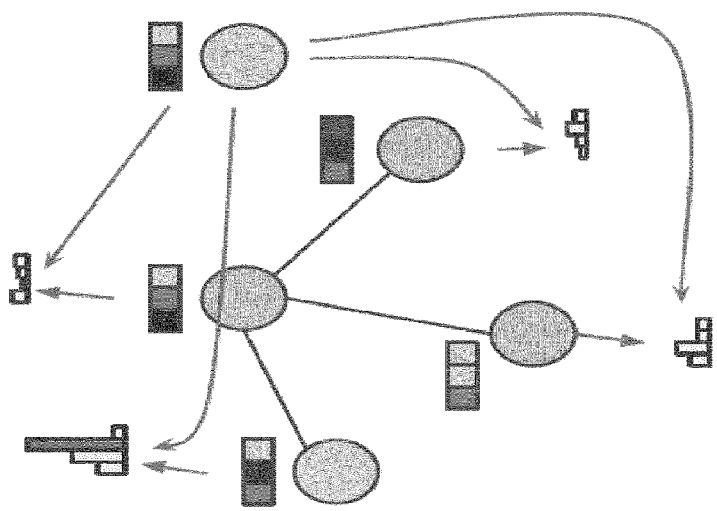
FIG. 6 is a schematic illustration showing operation of the system of FIG. 1.
Figure 6:
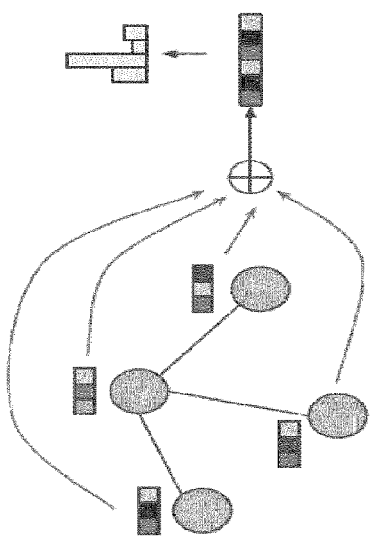
Figure 6:
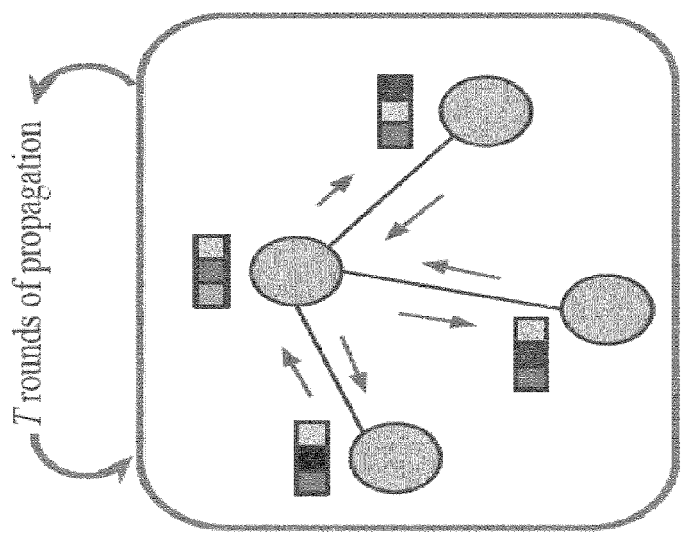

Referring now to FIG. 5, exemplary processing for updating node state vectors based upon information propagation will now be described. A schematic illustration of the information propagation process is shown in FIG. 6. Information propagation provides nodes with information regarding its local neighborhood. Changes in the structure of the graph or properties of the graph may be communicated to nodes through information propagation.

At step S501, a message vector is generated for each edge of the graph. The message vector may be generated based upon the node state vectors associated with the two nodes connected by the respective edge. Additionally, the message vector may further be generated based upon a feature vector associated with the respective edge if for example, edges are typed. The node state vectors and the edge feature vector may be processed by an edge neural network to generate the message vector.

At step S502, for each node, the message vectors associated with incoming edges are aggregated. It will be appreciated that aggregation of message vectors associated with outgoing edges is also possible and that the aggregated message vector may be an aggregation of the message vectors associated with either incoming edges, outgoing edges or every edge connected to a node. The aggregation may be a summation of the message vectors or any other method of aggregation as deemed suitable a person skilled in the art.

At step S503, the node state vector associated with each node is updated based upon the respective aggregated message vector determined at step S502. An updated node state vector for a respective node may be generated based upon processing, by a node neural network, of the respective aggregated message vector and the current node state vector to generate an updated node state vector.

The message generating neural network of step S502 and the neural network for updating node state vectors may be forward feedforward neural networks such as an MLP or recurrent neural networks such as an LSTM or GRU.

At step S504, it is determined whether or not further rounds of information propagation are required. A single round of information propagation will enable a node to obtain information regarding its local neighborhood whilst further rounds of information propagation will enable a node to obtain information from further afield in the graph.

If a further round of information propagation is required, processing returns to step S501. Alternatively, if no further rounds of information propagation are required, the updated node state vectors may be output at step S505.

By using information propagation, node state vectors may comprise information relating to the structure of the graph. Use of node state vectors in the sequential graph generating process enables decisions to be made based upon the structure of the graph and the sequence of decisions. By contrast, a conventional recurrent neural network modelling the graph as sequence of node/edge generating decision relies only upon the sequence of decisions and lacks the ability to incorporate structural information of the graph or to refer to specific nodes in its decision making process.

An exemplary implementation of the above information propagation process will now be described in more detail. The message vector of step S501 may be generated according to the following:

$$m_{u \to v} = f_e(h_u, h_v, x_{u,v}) = \text{MLP}(\text{concat}([h_u, h_v, x_{u,v}]))$$

where $m_{u \to v}$ is the message vector associated with an edge connecting a node u and a node v, $f_e$ is a message generating function which is implemented using a fully connected neural network, MLP, $h_u$ is a node state vector associated with node u, $h_v$ is a node state vector associated with node v, $x_{u,v}$ is a feature vector associated with the edge and concat is an operation concatenating its operands into a single vector.

If message vectors are to be generated in the reverse (outgoing) direction, then an additional MLP having the same form as above may be used for generating message vectors in the reverse direction:

$$m'_{u \to v} = f'_e(h_u, h_v, x_{u,v}) = \text{MLP}'(\text{concat}([h_u, h_v, x_{u,v}]))$$

The additional neural network, MLP', for the reverse direction may also share some or all of the parameters of the MLP for the incoming direction. Both MLPs may have linear activation functions.

For a particular node v, aggregating the message vectors, corresponding to step S502, may be performed as follows:

$$a_v = \sum_{u:(u,v) \in E} m_{u \to v}$$

or as follows if both incoming and outgoing message vectors are to be used:

$$a_v = \sum_{u:(u,v) \in E} m_{u \to v} + \sum_{u:(u,v) \in E} m'_{u \to v}$$

where $a_v$ is the aggregated message vector for node v and E is the set of edges of the graph. As can be seen, the above aggregation is a summation of the message vectors associated with the incoming and/or outgoing edges connected to node v.

As described above, at step S503, the node state vector for a respective node may be updated based upon processing the aggregated message vectors using a node neural network. For example, the node neural network may be implemented as a recurrent neural network, as follows:

$$h'_v = \text{RNNCell}(h_v, a_v)$$

The RNNCell may be a standard recurrent neural network type, in which case the update to the node state vector may be performed as:

$h'_v = \sigma(Wh_v + Ua_v)$ where σ is a sigmoid activation function and W and U are respective weight matrices.

Alternatively, the recurrent neural network may be a GRU type, in which case the update to the node state vector may be performed as:

$z_v = \sigma(W_z h_v + U_z a_v)$, $r_v = \sigma(W_z h_v + U_z a_v)$, $\tilde{h}_v = \tan h(W(r_v \odot h_v) + U a_v)$, $h'_v = (1 - z_v) \odot h_v + z_v \odot \tilde{h}_v$, where ⊙ is a gated sum.

Alternatively, the recurrent neural network may an LSTM type, in which case the update to the node state vector may be performed as:

$i_v = \sigma(W_i h_v + U_i a_v + V_i c_v)$, $f_v = \sigma(W_f h_v + U_f a_v + V_v c_v)$, $\tilde{c}_v = \tan h(W_c h_v + U_c a_v)$, $c'_v = f_v \odot c_v + i_v \odot \tilde{c}_v$, $o'_c = \sigma(W_o h_v + U_o a_v + V_o c'_v)$.

$h'_v = o'_v \odot \tan h(c'_v)$.

where each V is a respective weight matrix.

As discussed above, a graph state vector may be determined based upon the node state vectors (whether updated or not). Given that a graph will generally contain more information than individual nodes, the graph state vector may be of higher dimensionality than a node state vector. A node state vector may be mapped to a vector of higher dimensionality based upon processing the node state vector using a neural network. The graph state vector may then be obtained by aggregating the higher dimensional node state vectors. Alternatively, if mapping to a higher dimensional vector is not performed, the graph state vector may be an aggregation of the node state vectors.

The aggregation to generate a graph state vector may be based upon a gated sum. For example, a gating neural network comprising a final sigmoid activation function layer and one or more lower layers may be used to process a node state vector (irrespective of dimensionality) to obtain a set of gating weights associated with of the node state vector. The set of gating weights may comprise a weight for each element of the node state vector. The aggregation may be based upon a sum of the node state vectors having their corresponding gating weights applied.

For example, mapping a node state vector to a higher dimensional node state vector may be implemented as follows:

$h_v^G = f_m(h_v)$ where $f_m$ is a function mapping to a higher dimensional space implemented as an MLP. The MLP may have a linear activation function. The dimensionality of $h_v^G$ may, for example, be twice the dimensionality of $h_v$.

The graph state vector may be computed as a gated sum of the higher dimensional node state vectors as follows:

$h_G = \sum_{v \in V} g_v^G \odot h_v^G$ $g_v^G = \sigma(g_m(h_v))$ where V is the set of nodes of the graph, $g_m$ is an MLP having a linear activation function which feeds into an output layer having a sigmoid activation function to produce a set of weights $g_v^G$ for node v.

An exemplary implementation of the node creation neural network 101 will now be described in more detail and is schematically illustrated in FIG. 6. As discussed above, the node creation neural network 101 outputs one or more probabilities of adding a new node to a graph and may be implemented as follows:

$p(\text{add one more node}|G) = \sigma(f_{an}(h_G))$ where $f_{an}$ is an MLP having a linear activation function the output of which is fed into a layer having a sigmoid activation function denoted by σ, and $h_G$ is a graph state vector. Where nodes may be one of K types, the output of $f_{an}$ may be a K+1 dimensional vector representing a score for adding a node of each type and also a score for not adding a node. The sigmoid layer above may be replaced with a softmax layer to convert the scores to probabilities as shown below:

$\hat{p} = [\hat{p}_1, \ldots, \hat{p}_{K+1}]^T = f_{an}(h_G)$ $p_k = \frac{\exp(\hat{p}_k)}{\sum_{k'} \exp(\hat{p}_{k'})}, \forall k$ where $\hat{p}_k$ is a score for node type k and $p_k$ is the probability of adding a node of type k.

An exemplary implementation of the edge addition neural network 102 will now be described in more detail. The schematic illustration of FIG. 6 also applies. One possible implementation has a similar form to the exemplary implementation of the node creation neural network 101 and is implemented as follows:

$p(\text{add edge}|G, v) = \sigma(f_{ae}(h_G, h_v^{(T)}))$ where $f_{ae}$ is an MLP having a linear activation function the output of which is fed into a layer having a sigmoid activation function denoted by σ, $h_G$ is a graph state vector and $h_v^{(T)}$ is an updated node state vector of a candidate node v 107 after T rounds of information propagation. In this implementation, the output of the edge addition neural network 102 is a probability of adding an edge connected to the candidate node 107 with edge typing handled by the node selection neural network 103. However, it will be appreciated that edge typing may be handled by the edge addition neural network 102 in similar manner described above with respect to node types.

An exemplary implementation of the node selection neural network 103 will now be described in more detail and is schematically illustrated in FIG. 6. The node selection neural network 103 may firstly generate a score for each node of the graph to connect a candidate node 107 to as follows:

$s_u = f_s(h_u^{(T)}, h_v^{(T)}) = \text{MLP}(\text{concat}([h_u^{(T)}, h_v^{(T)}]))$ where $s_u$ is a score for selecting node u, $f_s$ is scoring function implemented by an MLP, $h_u^{(T)}$ is an updated node state vector for each node of the graph after performing T rounds of information propagation and $h_v^{(T)}$ is the updated node state vector for the candidate node v 107 after performing T rounds of information propagation. In this implementation, T=1 or 2 rounds of information propagation. However, it will be appreciated that further rounds of information may be performed if deemed appropriate by a person skilled in the art.

The scores may then be converted to a probability using a softmax layer:

$$p_u = \frac{\exp(s_u)}{\sum_{u'} \exp(s_{u'})}$$

where $p_u$ is the probability of selecting node u of the graph to connect to candidate node v 107.

Where edges are typed, for each node, a vector of scores comprising a score for each of J edge types may be computed. The softmax layer may then be computed over all scores across node and edge types:

$$p_{u,j} = \frac{\exp(s_{u,j})}{\sum_{u',j'} \exp(s_{u',j'})}$$

where $s_{u,j}$ is a score for connecting the candidate node v 107 to node u of the graph using edge type j and $p_{u,j}$ is the corresponding probability.

Any of the above probability distributions may be based upon a conditional probability distribution. That is, the graph generation process may be conditioned on some additional input. For example, the conditional probability distribution may be conditioned on data retrieved from a memory. The graph, for example, the graph state vector, may be used to query a memory to retrieve data from the memory. In addition, the conditioning may be based upon an attention mechanism.

The generative graph model and in particular the probability distributions represented by the one or more neural networks defines a joint distribution $p(G, \pi)$ over graphs G and node and edge orderings n. As will be appreciated from the above, generating a graph using the system 100 generates both a graph and a particular ordering of nodes and edges based upon the graph construction sequence. For training of the one or more neural networks, optimizing the logarithm of marginal likelihood $p(G) = \sum_{\pi \in P(G)} p(G, \pi)$ may be used. However, optimization of log $p(G)$ may be intractable for large graphs. Therefore, the one or more neural networks may be trained based upon optimizing an expected joint log-likelihood sampled from a training dataset of graphs as shown below:

$$\mathbb{E}_{p_{data}(G,\pi)}[\log p_{data}(G,\pi)] = \mathbb{E}_{p_{data}(G)} \mathbb{E}_{p_{data}(\pi|G)} [\log p(G,\pi)]$$

where $p_{data}(G)$ may be computed by sampling from the training dataset whilst $p_{data}(\pi|G)$ may be sampled from the training dataset or may be suitably chosen beforehand. For example, where there exists a canonical ordering associated with a graph of the training dataset, the distribution $p_{data}(\pi|G)$ may be based upon a delta function that places all of the probability on the canonical ordering.

The above training process enables the system to be train faster than a conventional recurrent neural network system and provides better optimization of the system.

The training dataset may comprise graphs that are structurally identical but having different permutations of their node and edge orderings. The permutations may be a random permutation of a canonical ordering or a random ordering generated from a uniform distribution or the ordering may be a learned ordering.

In an exemplary application of drug discovery, the "ChEMBL" database provided by the European Bioinformatics Institute of the European Molecular Biology Laboratory (EMBL-EBI) may be used to obtain exemplary drug molecules for the generation of a training dataset. A canonical ordering may be based upon the simplified molecular-input line-entry system (SMILES) representation associated with the molecule and a graph generated from the SMILES representation using a tool such as "RDKit: Open-source cheminformatics software" available at http://www.rdkit.org.

Evaluation of the learned graph generative model may be performed by computing the marginal likelihood. This may be performed using a sampling method such as importance sampling. For example, one Monte-Carlo estimate based on importance sampling is shown below:

$$p(G) = \sum_{\pi} p(G, \pi) = \sum_{\pi} q(\pi|G) \frac{p(G, \pi)}{q(\pi|G)} = \mathbb{E}_{q(\pi|G)} \left[ \frac{p(G, \pi)}{q(\pi|G)} \right]$$

where $q(\pi|G)$ is any proposal distribution over ordering permutations, and the estimate may be obtained by generating a few samples from $q(\pi|G)$ and then taking the average $$\frac{p(G, \pi)}{q(\pi|G)}$$

for the samples. Where there exists a canonical ordering associated with a graph, $q(\pi|G)$ may be based upon a delta function that places all of the probability on the canonical ordering.

FIG. 66 schematically illustrates operation of an example system of the type shown in FIG. 1. Thus on the left FIG. 6 shows a schematic illustration of a process for updating state vectors associated with nodes of the graph. In the center FIG. 6 shows a schematic illustration of a process for generating one or more probabilities based upon the graph, in particular graph level predictions for add node and add edge functions. On the right FIG. 6 shows a schematic illustration of a process for selecting a node.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system for generating a graph, the graph comprising a set of nodes and edges, the system comprising one or more computers and one or more storage devices storing instructions that when executed by the one or more computers cause the one or more computers to perform operations comprising:
generating, by the one or more computers, the graph by generating a sequence of decisions, each decision in the sequence being either a node generation decision or an edge generating decision, the generating comprising, for each decision:
generating, using a trained neural network system comprising one or more neural networks, an output representing a probability distribution over node generating decisions and/or edge generating decisions;
selecting the decision from the probability distribution represented by the output of the trained neural network system; and
generating an edge or node of the graph based on the decision.

2. The system of claim 1, wherein generating the graph comprises performing an iterative process that, at each iteration of the iterative process, generates an edge subsequent to generating a node.

3. The system of claim 1, wherein the probability distribution represented by the output of the trained neural network system is determined based upon a conditional probability distribution.

4. The system of claim 3, wherein one or more neural networks are conditioned on a conditioning input through an attention mechanism.

5. The system of claim 3, wherein the one or more neural networks are conditioned on a conditioning input that is retrieved from a memory.

6. The system of claim 1, wherein the one or more neural networks are trained based upon maximizing an expected log-likelihood of a training dataset of graphs.

7. The system of claim 6, wherein generating the output representing the probability distribution comprises, subsequent to completion of training of the one or more neural networks, adjusting an adjustable bias to alter a property associated with the graph.

8. The system of claim 1, wherein the graph represents the structure of a molecule, each respective node of the graph representing an atom of the molecule and each respective edge of the graph representing a chemical bond between atoms of the molecule.

9. The system of claim 8, wherein the one or more neural networks is trained based upon a metric comprising a chemical property.

10. The system of claim 1, wherein the sequence of decisions alternates between node generating decisions and edge generating decisions.

11. A method performed by one or more computers and for generating a graph, the graph comprising a set of nodes and edges, the method comprising:
generating, by the one or more computers, the graph by generating a sequence of decisions, each decision in the sequence being either a node generation decision or an edge generating decision, the generating comprising, for each decision:
generating, using a trained neural network system comprising one or more neural networks, an output representing a probability distribution over node generating decisions and/or edge generating decisions;

selecting the decision from the probability distribution represented by the output of the trained neural network system; and generating an edge or node of the graph based on the decision.

12. The method of claim 11, wherein generating the graph comprises performing an iterative process that, at each iteration of the iterative process, generates an edge subsequent to generating a node.

13. The method of claim 11, wherein the probability distribution represented by the output of the trained neural network system is determined based upon a conditional probability distribution.

14. The method of claim 13, wherein one or more neural networks are conditioned on a conditioning input through an attention mechanism.

15. The method of claim 13, wherein the one or more neural networks are conditioned on a conditioning input that is retrieved from a memory.

16. The method of claim 11, wherein the one or more neural networks are trained based upon maximizing an expected log-likelihood of a training dataset of graphs.

17. The method of claim 16, wherein generating the output representing the probability distribution comprises, subsequent to completion of training of the one or more neural networks, adjusting an adjustable bias to alter a property associated with the graph.

18. The method of claim 11, wherein the graph represents the structure of a molecule, each respective node of the graph representing an atom of the molecule and each respective edge of the graph representing a chemical bond between atoms of the molecule.

19. The method of claim 18, wherein the one or more neural networks is trained based upon a metric comprising a chemical property.

20. One or more non-transitory computer storage media storing instructions that when executed by one or more computers cause the one or more computers to perform operations for generating a graph, the graph comprising a set of nodes and edges, the operations comprising:

generating, by the one or more computers, the graph by generating a sequence of decisions, each decision in the sequence being either a node generation decision or an edge generating decision, the generating comprising, for each decision:

generating, using a trained neural network system comprising one or more neural networks, an output representing a probability distribution over node generating decisions and/or edge generating decisions;

selecting the decision from the probability distribution represented by the output of the trained neural network system; and generating an edge or node of the graph based on the decision.

* * * * *